US012654001B2

(12) United States Patent
Valentine

(10) Patent No.: US 12,654,001 B2
(45) Date of Patent: Jun. 16, 2026

(54) AUTOMATED EXTERNAL DEFIBRILLATION (AED) ELECTRODES

(71) Applicant: Defibtech, LLC, Guilford, CT (US)

(72) Inventor: Matt Valentine, Madison, CT (US)

(73) Assignee: Defibtech, LLC, Guilford, CT (US)

( * ) Notice: Subject to any disclaimer, the term of this patent is extended or adjusted under 35 U.S.C. 154(b) by 127 days.

(21) Appl. No.: 18/459,833

(22) Filed: Sep. 1, 2023

(65) Prior Publication Data

US 2024/0189579 A1 Jun. 13, 2024

Related U.S. Application Data

(60) Provisional application No. 63/387,280, filed on Dec. 13, 2022.

(51) Int. Cl.
*A61N 1/04* (2006.01)
*A61N 1/39* (2006.01)

(52) U.S. Cl.
CPC ........... *A61N 1/0496* (2013.01); *A61N 1/046* (2013.01); *A61N 1/3904* (2017.08)

(58) Field of Classification Search
CPC .... A61N 1/0496; A61N 1/046; A61N 1/3904; A61N 1/0492; A61N 1/3925
USPC ........................................................ 307/142
See application file for complete search history.

(56) References Cited

U.S. PATENT DOCUMENTS 4,848,353 A 7/1989 Engel
11,857,327 B2 * 1/2024 Whiting ................. A61N 1/046

2003/0055459 A1 * 3/2003 Lyster .................... A61N 1/046
607/5
2003/0195569 A1 10/2003 Swerdlow
2017/0056682 A1 * 3/2017 Kumar .................... A61N 1/046
2022/0001167 A1 * 1/2022 Kaib ..................... A61N 1/0484
(Continued)

FOREIGN PATENT DOCUMENTS

WO WO-2020106520 A1 * 5/2020 .......... A61N 1/3987
WO WO 2022/109549 5/2022

OTHER PUBLICATIONS

PCT, Written Opinion of the International Searching Authority, issued in PCT/US23/73287, Mar. 25, 2024.
(Continued)

*Primary Examiner* — Richard Tan
(74) *Attorney, Agent, or Firm* — David J. Powsner; Davis Malm D'Agostine, PC

(57) ABSTRACT

Aspects of the invention provide an AED electrode that utilizes an acrylic adhesive to physically secure and electrically couple the electrode to a victim, e.g., for purposes of delivering high-energy electrical discharges of 10-360 Joules with currents from 100 A to 2500 A. Use of such an acrylic adhesive for securing an electrode to a victim in AED electrodes according to these aspects of the invention has the benefit, among others, of extending their shelf life and, thereby, lowering the cost and associated burden of a deployed AED. Further aspects of the invention provide AEDs incorporating electrodes of the types described above. Still further aspects of the invention provide methods of fabricating such AEDs and/or electrodes. Yet still further aspects of the invention provide methods of defibrillating a victim (including, delivering energy of 10 Joules to in some cases up to 360 Joules with currents as high as 100 A to 2500 A) using such AEDs and/or electrodes.

20 Claims, 3 Drawing Sheets

(56) References Cited

U.S. PATENT DOCUMENTS

| 2022/0088371 | A1 | | 3/2022 | Freeman |
| 2024/0058613 | A1 | * | 2/2024 | Sullivan ............. A61N 1/36585 |
| 2024/0217202 | A1 | | 7/2024 | Casey et al. |

OTHER PUBLICATIONS

PCT, International Search Report, issued in PCT/US23/73287, Mar. 25, 2024.

* cited by examiner

AUTOMATED EXTERNAL DEFIBRILLATION (AED) ELECTRODES

This application claims the benefit of priority of U.S. Patent Application Ser. No. 63/387,280, entitled Automated External Defibrillation (AED) Electrodes, filed Dec. 13, 2022, the teachings of which are incorporated herein by reference.

TECHNICAL FIELD

The present invention relates to automated external defibrillators (AED(s)), and, more specifically, to the electrodes, which are part of the electrical circuit, that conducts shock energy from an AED into a victim's body.

BACKGROUND OF THE INVENTION

External defibrillators are emergency medical devices designed to supply a controlled electric shock to a victim's heart during cardiac arrest to reestablish an effective heart rhythm. This electric shock is delivered by electrodes that are electrically connected with the external defibrillator and in contact with the victim's body.

These portable external defibrillators, commonly known as automated external defibrillators (AEDs), including automatic and semi-automatic variants, have gained acceptance by those outside the medical profession and have been deployed in myriad locations outside of traditional medical settings.

Due to the lifesaving benefits of AEDs, more and more non-medical users are purchasing and deploying AEDs in their respective environments. This allows for a rescue attempt without the delay associated with bringing the victim to a medical facility or bringing a medical facility to the victim (e.g., a life support ambulance).

Individuals as well as businesses are purchasing and deploying AEDs. As time is of the essence during any rescue attempt, multiple AEDs may be purchased by any particular individual or user to allow placement at multiple locations. In the case of an individual, this could be on several floors of a home, and in the case of a business, this could be for placement throughout a facility (e.g., factory, office building, or large retail center). Thus, regardless of where the victim is within the home/facility, access to an AED would only be seconds, or no more than minutes, away.

AEDs are designed to be stored in locations for long durations, with minimal monitoring and maintenance, which provide for ready access. AED maintenance primarily focuses on replacement of AED consumables (e.g., batteries and electrodes), which are subject to degradation or depletion over time. Among such consumables are the electrodes, which have traditionally been subject to degradation.

In operation, AEDs (i) assure that electrodes are properly placed on the victim by measuring impedance using a very low current signal that is less than 100 microAmps and that is at 8 khz and 16 khz; (ii) determine whether the victim's heart is in a shockable rhythm by acquiring ECG measurements from a low current/low voltage signal on the order of 500 microVolts amplitude; and (iii) defibrillate the victim's heart by delivering energy which is 10 Joules to in some cases up to 360 Joules depending upon the victim (e.g., infant, pediatric or adult) with currents as high as 100 A to 2500 A.

The capturing and delivery of the signals and energy to and from the heart is accomplished by electrically connecting the AED to a victim by a pair of electrodes. To facilitate this, some form of temporary adhesive is used that both secures the electrodes to the victim and permits that electrical connection.

Currently, the temporary adhesive employed on AED electrodes is hydrogel-based. While this temporary adhesive is acceptable for obtaining the required impedance and ECG data and delivery of a defibrillation energy, the hydrogel-based adhesives present significant practical problems.

Electrodes using hydrogel adhesive must be packaged for storage so that the hydrogel does not dry out and become ineffective as an adhesive. Even with state-of-the-art packaging, packaged hydrogel electrodes have a shelf life of a mere couple of years. AED batteries, which are also a consumable, can be designed to have shelf lives that are many years longer.

Additionally, the short shelf life of hydrogel electrodes complicates AED manufacturing. This short shelf life makes the electrodes a just in time supply inventory supply item. Just in time manufacturing inventory supply items increase carrying cost and waste in AED manufacturing.

What is needed in the art is an AED electrode that has a longer shelf life. By having an electrode with a longer shelf life, the maintenance cost and burden of a deployed AED is reduced, and the AED manufacturing process is made less costly.

SUMMARY OF THE INVENTION

The foregoing objects are among those attained by the invention, aspects of which provide an AED electrode that utilizes an acrylic adhesive to physically secure and electrically couple the electrode to a victim, e.g., for purposes of delivering high-energy electrical discharges of 10-360 Joules with currents from 100 A to 2500 A. Use of such an acrylic adhesive for securing an electrode to a victim according to these aspects of the invention has the benefit, among others, of extending electrode shelf life and, thereby, lowering the cost and associated burden of a deployed AED.

Related aspects of the invention provide an AED electrode, e.g., of the type described above, in which the electrode is sized and/or otherwise configured to efficaciously deliver such high-energy electrical discharges to the victim. Still other related aspects of the invention provide an AED electrode in which the acrylic adhesive is a skin contact adhesive. Still other related aspects of the invention provide an AED electrode, e.g., of the type described above, in which the acrylic adhesive is embodied on a transfer tape. Yet still further aspects of the invention provide an AED electrode, e.g., of the type described above in which the acrylic adhesive is the Omin-Wave adhesive product (Product ID #FLX068983) of FLEXcon Company, Inc. of Massachusetts. Still yet other aspects of the invention provide an AED electrode, e.g., of the type described above, in which the acrylic adhesive couples low energy signals between the electrode from a victim.

Further aspects of the invention provide AEDs incorporating electrodes of the types described above. Still further aspects of the invention provide methods of fabricating such AEDs and/or electrodes. Yet still further aspects of the invention provide methods of defibrillating a victim (including, delivering energy of 10 Joules to in some cases up to 360 Joules with currents as high as 100 A to 2500 A) using such AEDs and/or electrodes.

These and other aspects and advantages of the invention will become apparent from the following detailed description and the accompanying drawings that illustrate by way of example the features of the invention.

BRIEF DESCRIPTION OF THE DRAWINGS

A more complete understanding of the invention may be attained by reference to the drawings, in which.

DETAILED DESCRIPTION OF EXEMPLARY EMBODIMENTS

Figure 1:
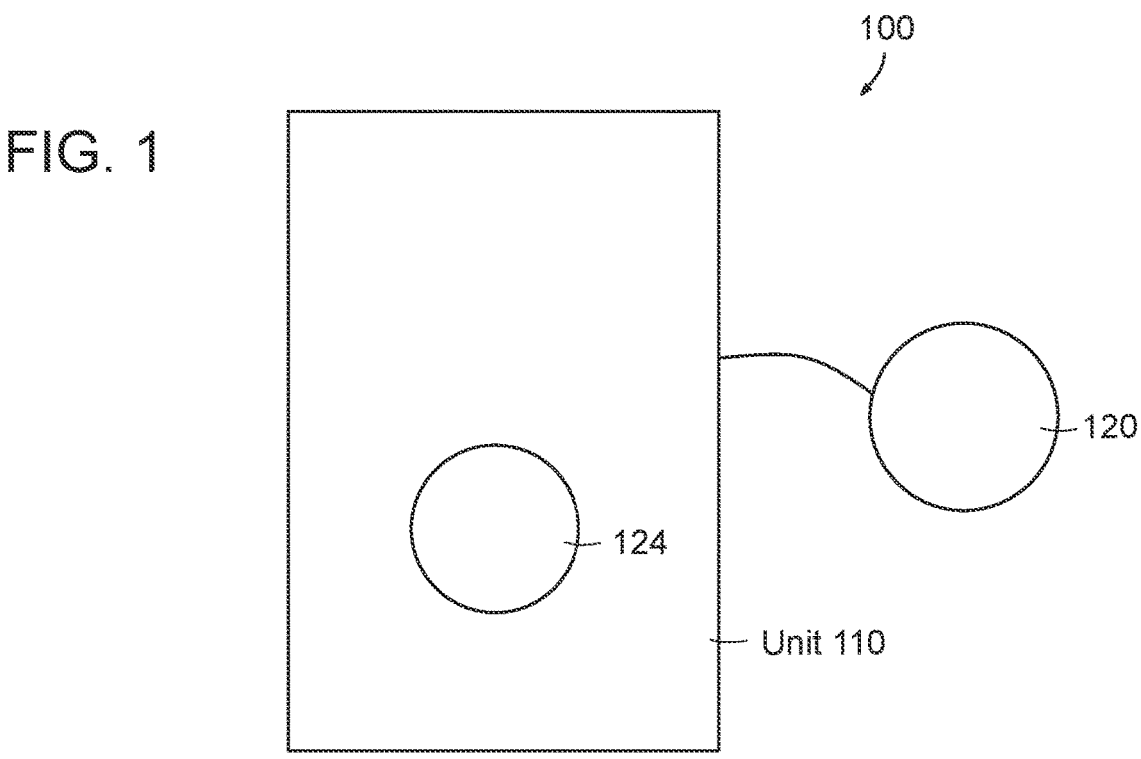
FIG. 1 is a front view of an illustrative AED system according to the invention.

Turning now to the drawings, FIG. 1 illustrates an AED system 100. As shown in FIG. 1, the AED system comprises an AED 110 and electrically connected thereto electrodes 120. More specifically, the AED includes at least a pair of electrodes, which are configured to be placed on a victim's chest or back (if the victim is a child). Depending on the type of AED, automatic or automated, if automated a shock button 124 is provided.

AED 110, which is of the type known in the art as adapted in accord with the teachings hereof, may include additional structure such as speakers, audio output jacks, a defined user interface, ON/OFF switch, a status indicator, card port for data storage, a universal serial bus (more commonly known as a USB port), standardized interface socket as well as other features. Some of these features may directly support the use of the AED, such as a speaker to communicate with a user of the AED, and others are optional. Many of the features that support a user are based on rescue protocols implemented by the AED.

Figure 2:
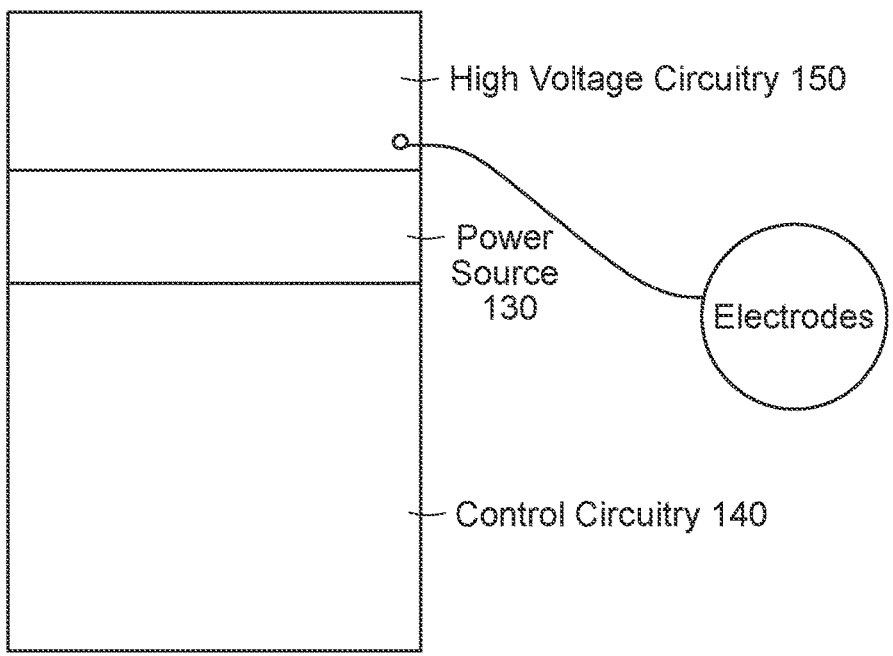
FIG. 2 is a view of the relevant structural areas of the illustrative AED shown in FIG. 1.

Referring now to FIG. 2, AED 110 includes three main functional units. The first is a power source 130. The second is control circuitry 140. The third is high voltage circuitry 150.

The power source 130 is generally a portable source such as a battery or several batteries, though, other power sources of the type known in the art for use with AEDs may be used in addition or instead, all as adapted in accord with the teachings hereof.

The control circuitry 140, which is powered by the power source 130, is of the conventional type known in the art as adapted in accord with the teachings hereof and includes, by way of non-limiting example, a main processor, for running AED programs, including control programming, stored in memory. Per convention in the art (as adapted in accord with the teachings hereof), the control circuitry obtains ECG signals from the electrodes and takes impedance measurements across the deployed electrodes, analyzes the obtained ECG signals to make a determination as to whether the AED should provide a shock to a victim and, if so, begins the shock sequence and provides the shock. The delivery of the shock may be controlled by the control circuitry or require a user to deliver the shock using a button or similar activation mechanism, all per convention in the art as adapted in accord with the teachings hereof.

The high voltage circuitry 150, which is of the conventional type known in the art as adapted in accord with the teachings hereof, generates the energy necessary to administer a shock, when so directed by the control circuitry or otherwise. When a shock is delivered, the shock energy is transmitted from the high voltage circuitry to the electrodes 120 which in turn is transmitted to the victim.

AED 110 and, more generally, AED system 100 operated in the conventional manner known in the art as adapted in accord with the teachings hereof.

Figure 3:
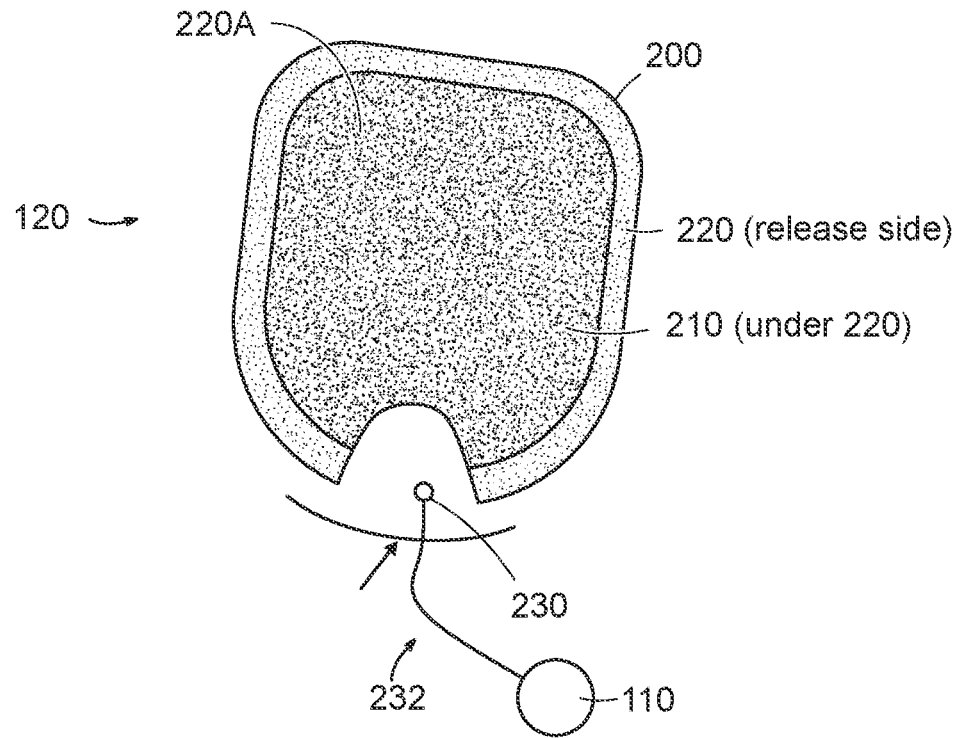
FIG. 3 is a side view of an AED electrode according to the invention.
Figure 4:
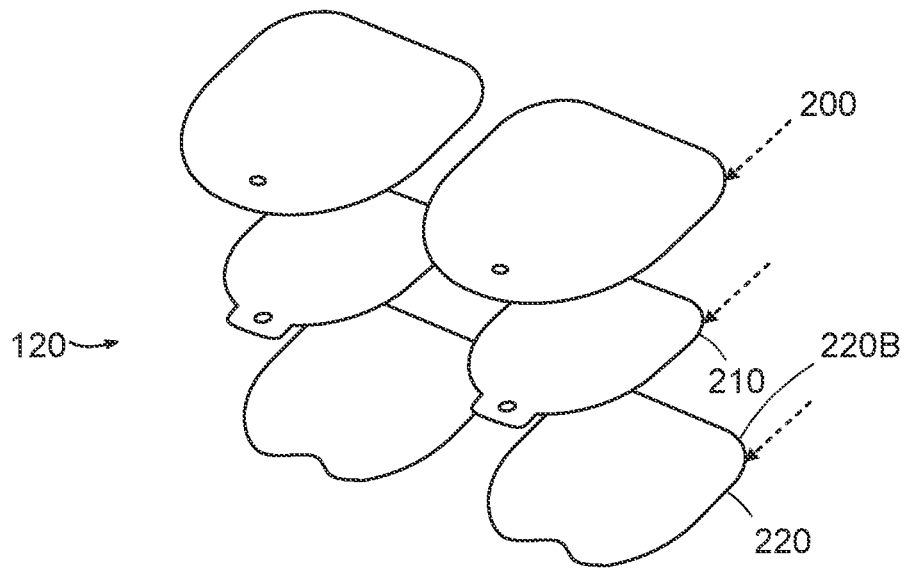
FIG. 4 is an exploded view of the AED electrode depicted in FIG. 3.

Continuing with FIG. 3, at least one (and, preferably, all) of the electrodes 120 includes a base 200 which has adhered to it a conductive layer 210, which in turn has an adhesive 220 adhered to the conductive layer. As shown, the conductive layer is ideally enclosed between the base and the adhesive layer. The enclosure of the conductive layer is further shown in FIG. 5, which shows, by way of non-limiting example, the measurements of the base (here, by way of non-limiting example, labelled "foam") in inches, the conductive layer (here, by way of example, "tin") and the adhesive (here, labelled "adhesive"). The base can be adhered to the conductive layer in a manner known in the art as adapted in accord with the teachings hereof.

Continuing with FIG. 3, the conductive layer 210 is electrically connected, such as by a rivet 230 and wire 232, to the AED 110. Such a wire may have a connector (not shown) for temporarily connecting the electrode to the AED to facilitate pad replacement.

Figure 5:
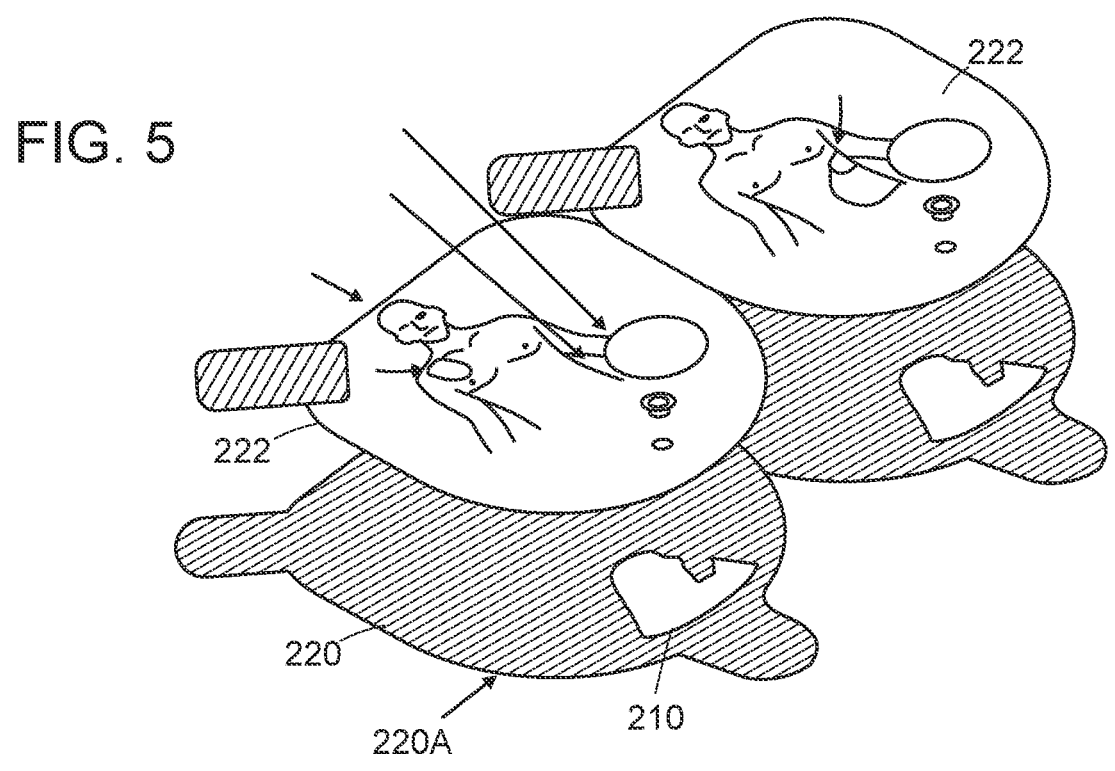
FIG. 5 is a top view of an AED electrode according to the invention showing the general measurements of various elements of the electrode.

The adhesive layer 220 has a first side 220A that is adherable to a victim's skin and a second side 220B that it adhered to the conductive layer 210 and, if required or desired, to secure the conductive layer to the base 200, which is accomplished by enveloping the conductive layer (see FIG. 5 for exemplary, relevant measurements). The adhesive layer has on the side being adhered to the conductive layer, and possibly to the base, a bonding adhesive which creates at least a semi-permanent bond with the conductive layer and, if applicable, the base. Preferably, the semi-permanent bond is at least stronger than the bond created between the adhesive layer and a victim's, such that when the electrode is removed from the victim's skin only a trace amount of the adhesive stays adhered to the electrode, all per convention in the art as adapted in accord with the teachings hereof.

The adhesive 220 is suitable for passing ECG signals from a victim to the conductive layer 210, passing impedance signals generated by the control system 140 to and from the conductive layer, and passing multiple shocks generated from the high voltage circuitry 150 from the conductive layer through the adhesive layer to a victim. The area of the electrode is in accordance with ANSI/.AAMI DF39; 199, section 201.108.7. Measurements of a typical AED pad used by the Applicant, Defibtech, L.L.C., are shown in FIG. 5 by way of non-limiting example.

Conductive layer 210, which is also sized in accordance with ANSI/.AAMI DF39; 1993, section 201.108.7 and may be made of any suitable conductive material, but tin is commonly used. Base layer 200, which is sized in accord with the foregoing, is of foam or other material (or combination thereof) conventional in the art as adapted in accord with the teachings hereof.

Continuing with FIG. 5, a typical area of the conductive layer 210 is approximately 77 cm2 giving a discharge density at 300 Joules, a potential adult requirement, of 4.6 Joules per cm2, which tends to set an approximate upper limit of energy density for AED pads. A typical electrode for measuring ECG signals which has a surface area of approximately 2 cm2 would have an energy density clearly exceeding 4.6 Joules per cm2 if used as an AED pad, which would be harmful to the victim and therefore not efficacious.

Figure 6:
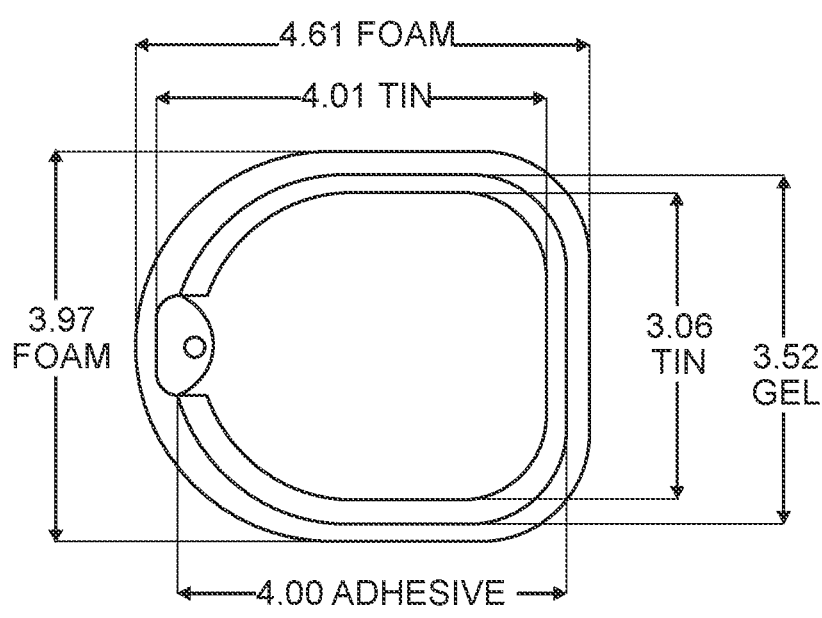
FIG. 6 is perspective view of an AED electrode according to the invention with a protective layer removed.

As shown in FIG. 6, the electrodes may further include a temporary protective layer 222 over the first surface 220A (i.e., the adhesive layer surface that adheres to a victim's skin) of the adhesive layer 220, to prevent inadvertent adhesion of the adhesive. The electrode 120 may further be packaged in a container or pouch (not shown).

In use, an electrode 120 is deployed by removing it from any packaging and removing any protective layer 222 over the adhesive and placing the first surface 220A on the victim's skin in an appropriate location. Generally, an AED utilizes two electrodes, and the electrode placement is such that both receive ECG signals and deliver shock energy. For a typical adult, one electrode is placed on the victim's in the left upon quadrant of the chest and the second placed in the lower right quadrant. For a child, one electrode may be placed on the back and the other on the chest.

As previously indicated, the electrodes both conduct low energy signals from the victim to the AED 110 and high energy from the AED to the victim. Thus, in operation, the AED initially passes the low energy signal through the adhesive 220 to the conductive layer 210 which in turn conducts it to the AED for analysis. If the analysis of the received signal indicates a shock is advised, the AED will discharge a high energy burst to the signal receiver, through the adhesive to the victim.

The inventors have discovered that acrylic adhesives are not only capable of conducting the necessary low energy signals from the heart and between the electrodes but are also capable of conducting high energy electrical discharges, e.g., a shock, from a medical device (i.e., the AED 110) to a victim without harm to the victim. A suitable adhesive for practice of the invention is an acrylic adhesive for an electrode includes an organic polar salt that is pressure sensitive having a conductive matrix Even though the electrode is considered a consumable, the adhesive must remain viable to accommodate multiple shocks during a given rescue. Ideally, the adhesive should be biocompatible in accordance with a biocompatible standard such as ISO-10993. One acrylic adhesive used in practice of the invention is the OMNI-WAVE adhesive, a commercially available product of FLEXcon Company, Inc. of Massachusetts, Product ID #FLX068983, e.g., as described in the product Data Sheet entitled "Skin Contact Applications—Electrodes & Wearables—Hydrogel-Free Bio-Signal Sensing Transfer Tape," dated Nov. 10, 2022, available from that company, the teachings of which publication are incorporated herein by reference, and further described at https://www.flexcon-.com/product-finder/product/68983/omniwave-tt-200-black-h502-150-poly-h9-44pp8, the teachings of which are also incorporated herein by reference.

Other characteristics of the electrode 120 and adhesive used thereof are provided above, in the Summary of the Invention.

While certain example or illustrative examples have been described, these examples have been presented by way of example only and are not intended to limit the scope of the inventions disclosed herein. Indeed, the novel methods and systems described herein may be embodied in a variety of other forms.

In view of the foregoing, what is claimed is:

1. A method for manufacturing an automated external defibrillator (AED) electrode for use in an AED system for delivering a defibrillation shock of a defined shock energy in Joules to a victim comprising:

obtaining a base which is conductive having a surface area such that the shock energy per $cm^2$ does not exceed 5 Joules per $cm^2$;

obtaining a dry adhesive wherein the dry adhesive is signal and electrically conductive of at least impedance signals, electrocardiogram (ECG) signals and defibrillation energy and suitable for adhesion to the victim's skin;

adhering the dry adhesive to the base;

wherein the AED electrode delivers the defibrillation shock to the victim through the dry adhesive, and wherein the defibrillation shock delivered through the dry adhesive has a defined energy of between 10-360 Joules.

2. The method of claim 1 wherein the dry adhesive adhesion to the victim's skin will remain effective after four defibrillation discharges.

3. The method of claim 2 wherein each of the defibrillation discharges exceeds 50 Joules.

4. The method of claim 1 further including the steps of obtaining a protective covering, the protective covering being only temporarily adherable to the dry adhesive, and adhering the protective covering to the dry adhesive.

5. The method of claim 1 wherein the dry adhesive is an acrylic incorporating organic polar salt and a conductive matrix.

6. The method of claim 5 wherein the dry adhesive is pressure sensitive.

7. An automated external defibrillator (AED) system for delivering a defibrillation shock to a victim comprising:

A. the AED system capable of delivering the defibrillation shock;

B. a set of electrodes electrically connected to the AED system, each electrode of the set of electrodes having (i) a dry adhesive having a first side and a second side;

(ii) the dry adhesive capable of conducting at least impedance signals, electrocardiogram (ECG) signals and defibrillation energy; and (iii) a conductive base, wherein the dry adhesive is adhered on the first side to the conductive base and the second side is capable of being releasably adhered to the victim's skin, wherein the set of electrodes delivers the defibrillation shock to the victim through the dry adhesive, wherein the defibrillation shock delivered through the dry adhesive is between 10-360 Joules, and wherein the conductive base has a surface area such that an energy per $cm^2$ delivered by said each electrode during delivery of the defibrillation shock does not exceed 5 Joules per $cm^2$.

8. A method for delivering a defibrillation shock to a victim comprising the steps of:

identifying the victim potentially in cardiac arrest;

obtaining an automated external defibrillator (AED) having a set of electrodes wherein the set of electrodes are comprised of a dry adhesive capable of conducting at least impedance signals, electrocardiogram (ECG) signals and defibrillation energy;

adhering the set of electrodes to the victim; and if the victim is in the cardiac arrest, as determined by the AED, delivering the defibrillation shock to the victim, wherein the set of electrodes delivers the defibrillation shock to the victim through the dry adhesive, wherein the defibrillation shock delivered through the dry adhesive is between 10-360 Joules, and wherein each electrode of the set of electrodes has a surface area such that an energy per cm$^2$ delivered by said each electrode during delivery of the defibrillation shock does not exceed 5 Joules per cm$^2$.

9. An automated external defibrillator (AED) electrode that utilizes an acrylic adhesive to physically secure and electrically couple the AED electrode to a victim and that delivers to the victim through the acrylic adhesive high-energy electrical discharges, wherein the high-energy electrical discharges delivered through the acrylic adhesive are in a range of 10-360 Joules, wherein the acrylic adhesive is capable of conducting at least impedance signals, electrocardiogram (ECG) signals and defibrillation energy, and wherein the AED electrode has a surface area such that an energy per cm$^2$ per electrical discharge does not exceed 5 Joules per cm$^2$.

10. The AED electrode of claim 9, in which the AED electrode is sized and/or otherwise configured to efficaciously deliver such high-energy electrical discharges to the victim.

11. The AED electrode of claim 9 in which the acrylic adhesive is a skin contact adhesive.

12. The AED electrode of claim 9 in which the acrylic adhesive is embodied on a transfer tape.

13. The AED electrode of claim 9 in which the acrylic adhesive is an Omin-Wave adhesive product (Product ID #FLX068983) of FLEXcon Company, Inc. of Massachusetts.

14. The AED electrode of claim 9, in which the acrylic adhesive is adapted to low energy signals to the AED electrode from the victim.

15. An automated external defibrillator (AED) having one or more AED electrodes, where each such AED electrode utilizes an acrylic adhesive to physically secure and electrically couple the AED electrode to a victim and that delivers to the victim through the acrylic adhesive high-energy electrical discharges, wherein the high-energy discharges delivered through the acrylic adhesive are in a range of 10-360 Joules, and where the acrylic adhesive is capable of conducting at least impedance signals, electrocardiogram (ECG) signals and defibrillation energy.

16. The AED of claim 15, in which one or more of the AED electrodes is sized and/or otherwise configured to efficaciously deliver such high-energy electrical discharges to the victim.

17. The AED of claim 15, in which the acrylic adhesive is a skin contact adhesive.

18. The AED of claim 15 in which the acrylic adhesive is embodied on a transfer tape.

19. The AED of claim 15 in which the acrylic adhesive is an Omin-Wave adhesive product (Product ID #FLX068983) of FLEXcon Company, Inc. of Massachusetts.

20. The AED of claim 15, in which the acrylic adhesive is adapted to deliver low energy signals to the one or more AED electrodes from the victim.

* * * * *